(12) United States Patent
Ye et al.

(10) Patent No.: US 11,872,549 B2
(45) Date of Patent: *Jan. 16, 2024

(54) FLUIDIZED BED REACTOR, DEVICE, AND USE THEREOF (71) Applicant: DALIAN INSTITUTE OF CHEMICAL PHYSICS, CHINESE ACADEMY OF SCIENCES, Dalian (CN)

(72) Inventors: Mao Ye, Dalian (CN); Tao Zhang, Dalian (CN); Jinling Zhang, Dalian (CN); Shuliang Xu, Dalian (CN); Hailong Tang, Dalian (CN); Xiangao Wang, Dalian (CN); Cheng Zhang, Dalian (CN); Jinming Jia, Dalian (CN); Jing Wang, Dalian (CN); Hua Li, Dalian (CN); Chenggong Li, Dalian (CN); Zhongmin Liu, Dalian (CN)

(73) Assignee: DALIAN INSTITUTE OF CHEMICAL PHYSICS, CHINESE ACADEMY OF SCIENCES, Dalian (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/784,650

(22) PCT Filed: Oct. 16, 2020

(86) PCT No.: PCT/CN2020/121556
§ 371 (c)(1),
(2) Date: Jun. 12, 2022

(87) PCT Pub. No.: WO2022/077454
PCT Pub. Date: Apr. 21, 2022

(65) Prior Publication Data
US 2023/0001371 A1 Jan. 5, 2023

(51) Int. Cl.
B01J 8/26 (2006.01)
B01J 8/18 (2006.01)
(Continued)

(52) U.S. Cl.
CPC ........... *B01J 8/1809* (2013.01); *B01J 8/0065* (2013.01); *B01J 8/1836* (2013.01); *B01J 8/1863* (2013.01);
(Continued)

(58) Field of Classification Search
CPC ........ B01J 8/00; B01J 8/18; B01J 8/26; C07C 1/22; C10G 3/00
See application file for complete search history.

(56) References Cited

U.S. PATENT DOCUMENTS 10,710,940 B2 7/2020 Zhang et al.

FOREIGN PATENT DOCUMENTS

CN 101279873 A 10/2008
CN 202478902 U 10/2012
(Continued)

*Primary Examiner* — Sharon Pregler
(74) *Attorney, Agent, or Firm* — Bayramoglu Law Offices LLC (57) ABSTRACT A fluidized bed reactor includes a main shell and a coke control zone shell; the main shell includes an upper shell and a lower shell; the upper shell encloses a gas-solid separation zone, and the lower shell encloses a reaction zone; the reaction zone axially communicates with the gas-solid separation zone; the coke control zone shell is circumferentially arranged on an outer wall of the main shell; the coke control zone shell and the main shell enclose an annular cavity, and the annular cavity is a coke control zone; n baffles are radially arranged in the coke control zone, and the n baffles divide the coke control zone into n coke control zone subzones, where n is an integer; the coke control zone subzones are provided with a coke control raw material (Continued)

inlet; and a catalyst circulation hole is formed in each of n−1 of the baffles.

20 Claims, 2 Drawing Sheets

(51) Int. Cl.
    *B01J 8/00* (2006.01)
    *C07C 1/22* (2006.01)
    *C10G 3/00* (2006.01)

(52) U.S. Cl.
    CPC .................................... *B01J 8/26* (2013.01); *C07C 1/22* (2013.01); *C10G 3/60* (2013.01); *B01J 2208/00707* (2013.01); *B01J 2208/00938* (2013.01); *B01J 2208/00991* (2013.01); *C07C 2529/85* (2013.01); *C10G 2300/4075* (2013.01)

(56) References Cited

FOREIGN PATENT DOCUMENTS

| | | |
|---|---|---|
| CN | 104610006 A | 5/2015 |
| CN | 104672040 A | 6/2015 |
| CN | 104672044 A | 6/2015 |
| CN | 108786670 A | 11/2018 |
| CN | 110818521 A | 2/2020 |
| CN | 110818522 A | 2/2020 |
| CN | 111099945 A | 5/2020 |
| EA | 000819 B1 | 4/2000 |
| EA | 009015 B1 | 10/2007 |
| ES | 2298013 A1 | 5/2008 |
| JP | 2017501989 A | 1/2017 |
| JP | 2017504654 A | 2/2017 |
| RU | 2520487 C2 | 6/2014 |
| WO | 0117977 A1 | 3/2001 |
| WO | 2015077142 A1 | 5/2015 |
| WO | 2015081489 A1 | 6/2015 |
| WO | WO-2015081489 A1 * 6/2015 | .............. B01J 29/90 |

* cited by examiner

FLUIDIZED BED REACTOR, DEVICE, AND USE THEREOF

CROSS REFERENCE TO THE RELATED APPLICATIONS

This application is the national phase entry of International Application No. PCT/CN2020/121556, filed on Oct. 16, 2020, the entire contents of which are incorporated herein by reference.

TECHNICAL FIELD

The present application relates to a fluidized bed reactor, a device for preparing low-carbon olefins from an oxygen-containing compound, and use thereof, and belongs to the technical field of chemical equipment.

BACKGROUND

Methanol-to-olefin technology (MTO) mainly includes DMTO (methanol-to-olefin) technology of Dalian Institute of Chemical Physics, Chinese Academy of Sciences and MTO technology of UOP Company of the United States. In 2010, the Shenhua Baotou methanol-to-olefin plant using DMTO technology was completed and put into operation. This is the world's first industrial application of MTO technology. As of the end of 2019, 14 DMTO industrial plants have been put into production, with a total production capacity of about 8 million tons of low-carbon olefins per year.

In recent years, DMTO technology has been further developed, and a new generation of DMTO catalyst with better performance have gradually begun industrial applications, creating higher benefits for DMTO plants. The new generation of DMTO catalyst has higher methanol processing capacity and low-carbon olefin selectivity. It is difficult for the existing DMTO industrial devices to take full advantage of the advantages of the new generation of DMTO catalyst. Therefore, it is necessary to develop a DMTO device and production method that can meet the needs of a new generation of DMTO catalyst with high methanol processing capacity and high selectivity of low-carbon olefins.

SUMMARY

According to a first aspect of the present application, a fluidized bed reactor is provided, which can control the coke content, coke content distribution, and coke species in a dimethyl ether/methanol to olefins (DMTO) catalyst, thereby controlling the performance of the DMTO catalyst and improving the selectivity for low-carbon olefins.

The low-carbon olefins mentioned in the present application refer to ethylene and propylene.

The fluidized bed reactor includes a main shell and a coke control zone shell; the main shell includes an upper shell and a lower shell; the upper shell encloses a gas-solid separation zone, and the lower shell encloses a reaction zone; the reaction zone axially communicates with the gas-solid separation zone; the coke control zone shell is circumferentially arranged on an outer wall of the main shell; the coke control zone shell and the main shell enclose an annular cavity, and the annular cavity is a coke control zone; n baffles are radially arranged in the coke control zone, and the n baffles divide the coke control zone into n coke control zone subzones, where n is an integer; the coke control zone subzones are provided with a coke control raw material inlet; and a catalyst circulation hole is formed in each of n−1 of the baffles, such that a catalyst entering the coke control zone flows in an annular direction.

When there is only one zone in the coke control zone, a residence time distribution of the catalyst entering the coke control zone is similar to a residence time distribution of a completely-mixed tank reactor, and under such conditions, the obtained coke controlled catalyst granules show poor coke content uniformity (that is, some catalyst granules have a low coke content and some catalyst granules have a high coke content), resulting in low average activity and low average selectivity of the catalyst. In the present application, a coke control zone is arranged and baffles are radially arranged in the coke control zone to divide the coke control zone into a plurality of coke control zone subzones, such that a residence time distribution of the catalyst entering the coke control zone can be controlled to make the coke controlled catalyst have narrow coke content distribution, high average activity, and high average selectivity. Moreover, the zone control is also beneficial to the control of the coke species and coke content in the coke controlled catalyst.

In the present application, the catalyst entering the coke control zone may be a fresh catalyst or a regenerated catalyst. Preferably, the catalyst may be a regenerated catalyst, such that both the regeneration and the coke control can be achieved on-line.

Optionally, in the coke control zone, the n baffles may include a $1^{st}$ baffle, and a $2^{nd}$ baffle to an $n^{th}$ baffle;
  no catalyst circulation hole may be formed in the $1^{st}$ baffle; the catalyst circulation hole may be formed in each of the $2^{nd}$ baffle to the $n^{th}$ baffle;
  a coke control zone catalyst inlet may be formed in a $1^{st}$ coke control zone subzone formed through division by the $1^{st}$ baffle and the $2^{nd}$ baffle;
  a coke controlled catalyst delivery pipe may be arranged in an $n^{th}$ coke control zone subzone formed through division by the $1^{st}$ baffle and the $n^{th}$ baffle, and an outlet of the coke controlled catalyst delivery pipe may be formed in the reaction zone;
  the coke control raw material inlet may be formed at bottoms of the coke control zone subzones, and the coke control raw material inlet may be a coke control zone distributor; and a coke control zone gas delivery pipe may be arranged at tops of the coke control zone subzones, and an outlet of the coke control zone gas delivery pipe may be formed in the gas-solid separation zone.

Specifically, one or more catalyst circulation holes can be formed in each of the baffles, which is not strictly limited in the present application. When a plurality of catalyst circulation holes are formed, relative positions of the catalyst circulation holes are not strictly limited in the present application. For example, the plurality of catalyst circulation holes may be arranged in parallel, or may be arranged randomly.

In the present application, a shape of the coke controlled catalyst delivery pipe is not strictly limited, as long as it is ensured that the coke controlled catalyst delivery pipe can deliver a coke controlled catalyst to the reaction zone. For example, the coke controlled catalyst delivery pipe can be an L-shaped pipe, and can also be in other suitable shapes.

Preferably, the coke controlled catalyst delivery pipe can be an L-shaped pipe, such that an outlet of the coke controlled catalyst delivery pipe is at a lower position in the reaction zone, and a coke controlled catalyst can efficiently contact and react with the raw material including the oxygen-containing compound entering from the reaction zone distributor, which prevents the coke controlled catalyst from entering the first stripper.

A coke control zone distributor may be arranged at bottoms of the coke control zone subzones.

Preferably, a coke control zone distributor may be arranged at a bottom of each of the coke control zone subzones. In this way, the coke control raw material can enter the coke control zone uniformly as a whole, such that the phenomenon of non-uniform distribution of the coke control raw material among the subzones can be avoided, and the coke content and coke content distribution in a catalyst can be well controlled.

A gas delivery pipe may be arranged at tops of the coke control zone subzones.

Preferably, a gas delivery pipe may be arranged at a top of each of the coke control zone subzones. In this way, a coke content distribution in a catalyst can be well controlled.

Optionally, n may have a value range of $2 \leq n \leq 10$.

Optionally, a reaction zone distributor may be further arranged at a bottom of the reaction zone; and the reaction zone distributor may be configured to feed a reaction raw material.

Specifically, in the present application, the reaction raw material may be a raw material with an oxygen-containing compound.

Optionally, the reaction zone may be provided with a fluidized bed reactor cooler, and a bottom of the reaction zone may be provided with a first stripper; an inlet of the first stripper may be formed inside the lower shell; an outlet of the first stripper may be formed outside the lower shell; an open end of the inlet of the first stripper may be located above an outlet end of the coke controlled catalyst delivery pipe; and the outlet end of the coke controlled catalyst delivery pipe may be located above the reaction zone distributor.

Specifically, an open end of a first stripper inlet pipe may be arranged above the outlet end of the coke controlled catalyst delivery pipe, such as to prevent a coke controlled catalyst coming out of the coke controlled catalyst delivery pipe from entering the first stripper inlet pipe.

The outlet end of the coke controlled catalyst delivery pipe may be arranged above the reaction zone distributor, such that the coke controlled catalyst can directly and efficiently react with a reaction raw material coming out of the reaction zone distributor.

Optionally, the gas-solid separation zone may be provided with a first gas-solid separation unit and a second gas-solid separation unit; a catalyst outlet pipe of the first gas-solid separation unit may penetrate through a top of the coke control zone and may be inserted in the $1^{st}$ coke control zone subzone (that is, the catalyst outlet pipe of the first gas-solid separation unit may be inserted into the $1^{st}$ coke control zone subzone through the coke control zone catalyst inlet); a gas outlet of the first gas-solid separation unit may be formed in the gas-solid separation zone; an inlet of the second gas-solid separation unit may be formed in the gas-solid separation zone; and a catalyst outlet end of the second gas-solid separation unit may be located in the reaction zone.

Preferably, the coke control zone gas delivery pipe may be located above the catalyst outlet end of the second gas-solid separation unit.

Optionally, a first gas collection chamber may be further arranged in an upper part of the gas-solid separation zone;
a gas outlet of the second gas-solid separation unit may communicate with the first gas collection chamber; and
the first gas collection chamber may further communicate with a product gas delivery pipe.

According to a second aspect of the present application, a device for preparing low-carbon olefins from an oxygen-containing compound is also provided, where the device includes a fluidized bed regenerator and the fluidized bed reactor described above.

Specifically, the device for preparing low-carbon olefins from an oxygen-containing compound provided in the present application is provided with a fluidized bed regenerator; the fluidized bed regenerator is used to regenerate a spent catalyst; and a regenerated catalyst is fed into the coke control zone to undergo coke control, and then enters the reaction zone to participate a catalytic reaction. In the present application, a catalyst can be subjected to on-line regeneration and on-line coke control, which improves the production efficiency.

Optionally, the fluidized bed regenerator may include a regenerator shell; the regenerator shell may include an upper regenerator shell and a lower regenerator shell; the upper regenerator shell may enclose a gas-solid separation zone, and the lower regenerator shell may enclose a regeneration zone; a spent catalyst inlet may be formed in the regenerator shell; and the spent catalyst inlet may communicate with a first stripper outlet pipe through a spent catalyst delivery pipe.

Optionally, a regeneration zone distributor may be further arranged at a bottom of the regeneration zone; and the regeneration zone distributor may be configured to feed a regeneration gas.

Optionally, a second stripper may be arranged at the bottom of the regeneration zone; an inlet of the second stripper may be formed inside the regenerator shell; an outlet of the second stripper may be formed outside the regenerator shell; the second stripper may communicate with a first gas-solid separation unit through a regenerated catalyst delivery pipe; and an open end of the inlet of the second stripper may be located above the regeneration zone distributor.

Optionally, a third gas-solid separation unit and a second gas collection chamber may be further arranged in the regenerator shell; the second gas collection chamber may be located at an inner top of the regenerator shell; a gas outlet of the third gas-solid separation unit may communicate with the second gas collection chamber; the second gas collection chamber may communicate with a flue gas delivery pipe; and a catalyst outlet end of the third gas-solid separation unit may be located above an open end of a second stripper inlet pipe.

According to a third aspect of the present application, a method for preparing low-carbon olefins from an oxygen-containing compound is also provided, including the on-line modification of a DMTO catalyst through a coke control reaction using the fluidized bed reactor described above, where the method includes the following step:

feeding a catalyst and a coke control raw material into the coke control zone, where the catalyst reacts with the coke control raw material while flowing in an annular direction along the coke control zone subzones to generate a product including a coke controlled catalyst, and the coke controlled catalyst is a modified DMTO catalyst.

Optionally, the catalyst may flow in an annular direction along the catalyst circulation hole on the baffles; and coke control raw material may enter the coke control zone subzones from the coke control zone distributor to react with the catalyst.

Specifically, while the catalyst flows in an annular direction along the catalyst circulation hole on the baffles, the coke control raw material enters the coke control zone subzones from the coke control zone distributor located below to contact the catalyst and control a coke content in the catalyst, and a resulting gas phase (including the unreacted coke control raw material) is delivered to the gas-solid separation zone through a gas delivery pipe above the coke control zone.

Optionally, the coke controlled catalyst prepared may enter the reaction zone through the coke controlled catalyst delivery pipe, and then contact and react with a raw material including the oxygen-containing compound fed through the reaction zone distributor to generate a stream A with low-carbon olefins and a spent catalyst; and the product may further include a coke control product gas, and the coke control product gas may enter the gas-solid separation zone through the coke control zone gas delivery pipe.

Optionally, the stream A may be mixed with the coke control product gas entering the gas-solid separation zone to produce a stream B;
the stream B may enter the second gas-solid separation unit to undergo gas-solid separation to obtain a gas-phase stream C and a solid-phase stream D;
the gas-phase stream C may be a low-carbon olefin-containing product gas; and
the solid-phase stream D may include a spent catalyst.

Optionally, the gas-phase stream C may enter the first gas collection chamber, and then enter a downstream working section through the product gas delivery pipe;
the solid-phase stream D may be returned to the reaction zone of the fluidized bed reactor; and
a catalyst in the reaction zone may enter the first stripper through an open end of a first stripper inlet pipe to undergo stripping, and then enter a downstream zone.

Specifically, the downstream zone may be a regenerator.

Optionally, the coke control raw material may include $C_1$-$C_6$ hydrocarbon compounds; and preferably, the hydrocarbon compounds may be at least one selected from the group consisting of $C_1$-$C_6$ alkanes and $C_1$-$C_6$ olefins.

Optionally, the coke control raw material may further include at least one selected from the group consisting of hydrogen, alcohol compound, and water; and
a proportion of a total mass of the alcohol compound and the water in a mass of the coke control raw material may be greater than or equal to 10 wt % and less than or equal to 50 wt %.

Optionally, the alcohol compound may be at least one selected from the group consisting of methanol and ethanol.

Optionally, the coke control raw material may include 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water; and
a total amount of the hydrocarbon compounds may be greater than 0%.

Optionally, the catalyst may include an SAPO molecular sieve;
a coke content in the catalyst may be less than or equal to 3 wt %;
a coke content in the coke controlled catalyst may be 4 wt % to 9 wt %; and
a quartile deviation of a coke content distribution in the coke controlled catalyst may be less than 1 wt %.

Specifically, in the present application, the coke content in the coke controlled catalyst is controlled at 4 wt % to 9 wt % through the arrangement of the coke control zone and the selection of the coke control process. Since the catalyst is powdery, the coke content in the catalyst refers to an average coke content in catalyst granules, but coke contents in different catalyst granules may actually be different. In the present application, the quartile deviation of the coke content distribution in the coke controlled catalyst granules can be controlled to be less than 1 wt %, such that the overall coke content distribution of the catalyst is narrow, thereby improving the activity of the catalyst and the selectivity for low-carbon olefins.

Optionally, coke species in the coke controlled catalyst may include polymethylbenzene and polymethylnaphthalene;
a total mass of the polymethylbenzene and the polymethylnaphthalene may account for greater than or equal to 70 wt % of a total mass of coke;
a mass of coke species with a molecular weight greater than 184 may account for less than or equal to 25 wt % of the total mass of coke; and
the total mass of coke may refer to a total mass of coke species.

In the present application, types and contents of coke species are also very important, which is also one of the objectives of control in the present application. In the present application, a total mass of the polymethylbenzene and the polymethylnaphthalene is controlled to be greater than or equal to 70 wt % of the total mass of coke through the arrangement of coke control and the selection of coke control process parameters to improve the activity of the catalyst and the selectivity for low-carbon olefins.

Optionally, a coke content in the spent catalyst may be 9 wt % to 13 wt %.

Optionally, the oxygen-containing compound may be at least one selected from the group consisting of methanol and dimethyl ether (DME).

Optionally, process conditions of the coke control zone may be as follows: apparent gas linear velocity: 0.1 m/s to 0.5 m/s; reaction temperature: 300° C. to 700° C.; reaction pressure: 100 kPa to 500 kPa; and bed density: 400 kg/m$^3$ to 800 kg/m$^3$.

Optionally, process conditions of the reaction zone may be as follows: apparent gas linear velocity: 0.5 m/s to 2.0 m/s; reaction temperature: 350° C. to 550° C.; reaction pressure: 100 kPa to 500 kPa; and bed density: 150 kg/m$^3$ to 500 kg/m$^3$.

According to a fourth aspect of the present application, a method for preparing low-carbon olefins is also provided, including preparing low-carbon olefins using the device described above;
the method for preparing low-carbon olefins includes the method described above;
the method for preparing low-carbon olefins further includes the following steps:
allowing a spent catalyst in the reaction zone to enter the fluidized bed regenerator and undergo a regeneration treatment to generate a regenerated catalyst, and allowing the regenerated catalyst to enter the coke control zone of the fluidized bed reactor and to contact and react with the coke control raw material.

Optionally, the method may include: allowing the spent catalyst in the reaction zone to enter the fluidized bed regenerator through the first stripper and the spent catalyst delivery pipe, and to contact and react with the regeneration gas to obtain a stream E with a flue gas and a regenerated catalyst; allowing the stream E to enter the third gas-solid separation unit to separate the flue gas and the regenerated catalyst; and allowing the separated regenerated catalyst to enter the coke control zone of the fluidized bed reactor through the second stripper, the regenerated catalyst delivery pipe, and the first gas-solid separation unit, and to contact and react with the coke control raw material.

Optionally, a coke content in the regenerated catalyst may be less than or equal to 3 wt %.

Optionally, the regeneration gas may be at least one selected from the group consisting of oxygen, nitrogen, water vapor, and air.

Optionally, the regeneration gas may include 0 wt % to 100 wt % of air, 0 wt % to 50 wt % of oxygen, 0 wt % to 50 wt % of nitrogen, and 0 wt % to 50 wt % of water vapor; and contents of the air, the oxygen, the nitrogen, and the water vapor may not be simultaneously zero.

Optionally, process conditions of the regeneration zone may be as follows: apparent gas linear velocity: 0.5 m/s to 2.0 m/s; regeneration temperature: 600° C. to 750° C.; regeneration pressure: 100 kPa to 500 kPa; and bed density: 150 kg/m$^3$ to 700 kg/m$^3$.

Possible beneficial effects of the present application:

(1) A major characteristic of a DMTO catalyst is that the low-carbon olefin selectivity in a methanol conversion process increases with the increase of a coke content in the catalyst. The low-carbon olefins mentioned in the present application refer to ethylene and propylene. The applicants have found through research that main factors affecting the activity of a DMTO catalyst and the selectivity for low-carbon olefins include coke content, coke content distribution, and coke species in the catalyst. Under the same average coke content in catalysts, the narrower the coke content distribution, the higher the selectivity and activity of low-carbon olefins. Coke species in a catalyst may include polymethyl aromatic hydrocarbons, polymethyl cycloalkanes, and the like, where polymethylbenzene and polymethylnaphthalene can promote the formation of ethylene. Therefore, the control of the coke content, coke content distribution, and coke species in a catalyst is the key to control the activity of the DMTO catalyst and improve the selectivity of low-carbon olefins.

The fluidized bed reactor in the present application is provided with a coke control zone, and the coke control zone is divided into a plurality of subzones by the baffles arranged in the coke control zone, such that a catalyst flows along the subzones one by one. A residence time distribution of the catalyst is controlled through the subzones to be narrow, such as to control a coke content distribution in the catalyst and make the coke content distribution narrow. Moreover, the coke content and coke species are also controlled. Therefore, the activity of the DMTO catalyst and the selectivity for low-carbon olefins are improved.

(2) In the method of the present application, a catalyst can only flow from an upstream subzone to a downstream subzone through the catalyst circulation holes on the baffles in the coke control zone, such that an average residence time of a catalyst in the coke control zone can be controlled to control a coke content in the catalyst; and the structure of n coke control zone subzones is adopted to control a residence time distribution of a catalyst (the residence time distribution is similar to n serially-connected completely-mixed tank reactors), and a catalyst with a narrow coke content distribution is obtained.

(3) The present application can control the conversion and generation of coke species in a catalyst. On the one hand, inactive large-molecule coke species remaining in a regenerated catalyst are converted into small-molecule coke species; and on the other hand, a coke control raw material can also enter the catalyst to generate highly-active small-molecule coke species, and the small-molecule coke species are mainly polymethylbenzene and polymethylnaphthalene, which can improve the selectivity for ethylene.

(4) With the method for on-line modification of a DMTO catalyst through a coke control reaction in the present application, a coke controlled catalyst with high coke content, narrow coke content distribution, and polymethylbenzene and polymethylnaphthalene as main coke species components can be obtained, that is, the regenerated catalyst with low selectivity for low-carbon olefins is converted into a coke controlled catalyst with high selectivity for low-carbon olefins.

(5) The regenerated catalyst in the present application can be directly used in the process of preparing low-carbon olefins from an oxygen-containing compound without a coke control treatment, and in this case, the selectivity for low-carbon olefins in an obtained product gas is 80 wt % to 83 wt %. When the regenerated catalyst in the present application is subjected to a coke control treatment and then used in the process of preparing low-carbon olefins from an oxygen-containing compound, the selectivity for low-carbon olefins in an obtained product gas is 93 wt % to 96 wt %.

(6) In the method of the present application, a high-temperature regenerated catalyst from the regenerator is first cooled in the coke control zone and then enters the reaction zone, that is, there is no local high-temperature zone in the reaction zone; and thus the raw material with an oxygen-containing compound has a low coking rate.

(7) The reaction zone of the fluidized bed reactor in the present application includes a fluidized bed reactor cooler, which can accurately control a temperature of the reaction zone.

LIST OF REFERENCE NUMERALS 1 represents a fluidized bed reactor; 1-1 represents a main shell; 1-2 represents a reaction zone distributor;

1-3 represents a fluidized bed reactor cooler; 1-4 represents a coke control zone distributor;

1-5 represents a baffle; 1-6 represents a first gas-solid separation unit;

1-7 represents a coke controlled catalyst delivery pipe; 1-8 represents a coke control zone gas delivery pipe;

1-9 represents a second gas-solid separation unit; 1-10 represents a first gas collection chamber;

1-11 represents a product gas delivery pipe; 1-12 represents a first stripper;
1-13 represents a spent catalyst slide valve; 1-14 represents a spent catalyst delivery pipe;
2 represents a fluidized bed regenerator; 2-1 represents a regenerator shell; 2-2 represents a regeneration zone distributor;
2-3 represents a third gas-solid separation unit; 2-4 represents a second gas collection chamber;
2-5 represents a flue gas delivery pipe; 2-6 represents a second stripper; 2-7 represents a regenerator cooler;
2-8 represents a regenerated catalyst slide valve; and 2-9 represents a regenerated catalyst delivery pipe.

DETAILED DESCRIPTION OF THE EMBODIMENTS

The present application will be described in detail below with reference to examples, but the present application is not limited to these examples.

Possible embodiments are described below.

In order to improve the performance of a DMTO catalyst, the present application provides a method for on-line modification of a DMTO catalyst through a coke control reaction, including the following steps:

a) a regenerated catalyst is delivered to a coke control zone;

b) a coke control raw material including hydrogen, methane, ethane, ethylene, propane, propylene, butane, butene, pentane, pentene, hexane, hexene, methanol, ethanol, and water is delivered to a coke control reactor;

(c) the coke control raw material contacts and reacts with the regenerated catalyst in the coke control reactor, such that the coke control raw material is coked on the regenerated catalyst, where a coked catalyst is called a coke controlled catalyst; a coke content in the coke controlled catalyst is 4 wt % to 9 wt %; coke species include polymethylbenzene and polymethylnaphthalene, and a total mass of the polymethylbenzene and the polymethylnaphthalene accounts for greater than or equal to 70 wt % of a total mass of coke; and a mass of coke species with a molecular weight greater than 184 accounts for less than or equal to 25 wt % of the total mass of coke; and d) the coke controlled catalyst is delivered to a methanol conversion reactor.

The regenerated catalyst may be a DMTO catalyst with a coke content of less than or equal to 3 wt %, and an active component of the DMTO catalyst may be an SAPO molecular sieve.

The coke control raw material may be composed of 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water, and a total content of methanol, ethanol, and water may be greater than or equal to 10 wt %.

A reaction temperature of the coke control reaction may be 300° C. to 700° C.

Figure 1:
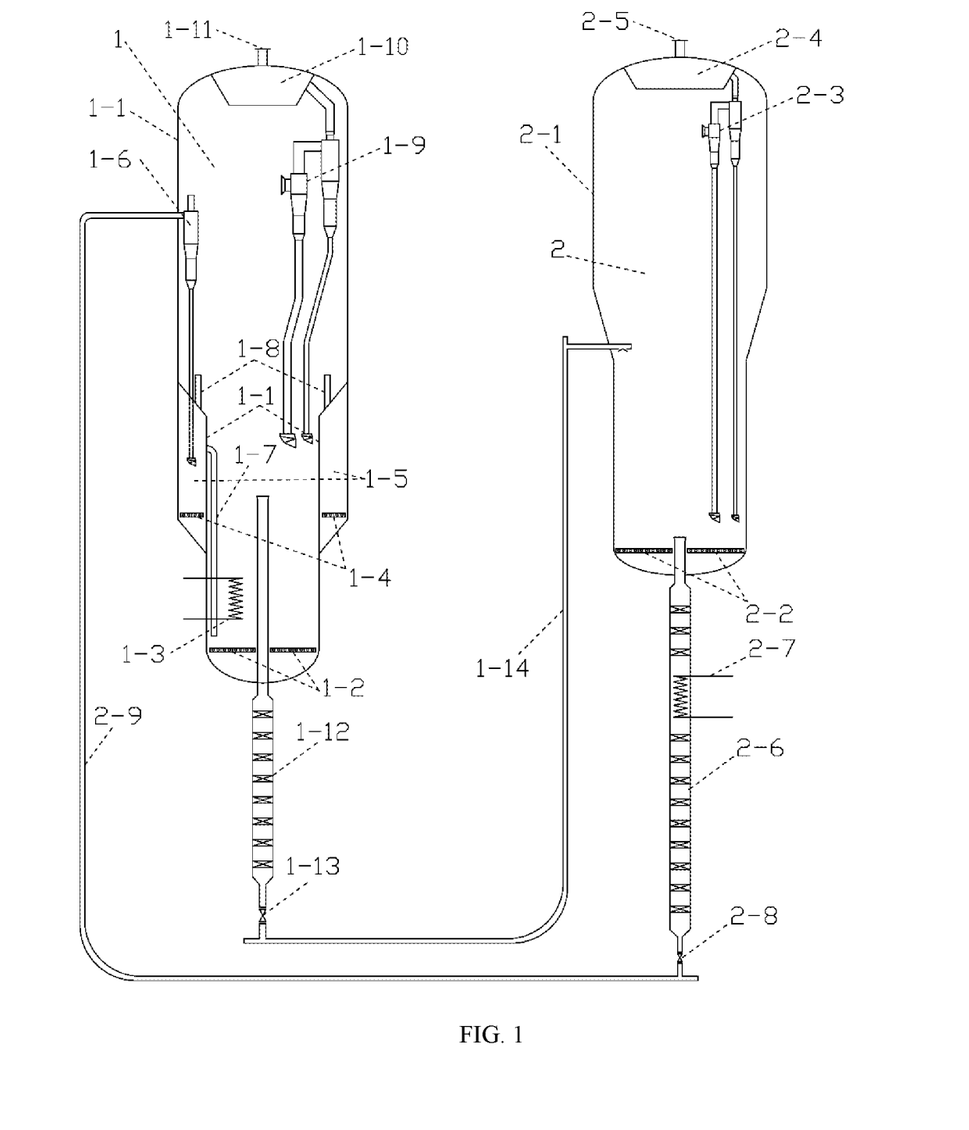
FIG. 1 is a schematic diagram of a DMTO device for preparing low-carbon olefins from an oxygen-containing compound according to an embodiment of the present application.

The present application also provides a method for preparing low-carbon olefins from an oxygen-containing compound that includes the method for on-line modification of a DMTO catalyst through a coke control reaction described above, and a device used thereby. The device includes a fluidized bed reactor 1 and a fluidized bed regenerator 2.

The fluidized bed reactor 1 is divided into a reaction zone, a coke control zone, and a gas-solid separation zone from bottom to top; the fluidized bed reactor 1 includes a fluidized bed reactor main shell 1-1, a reaction zone distributor 1-2, a fluidized bed reactor cooler 1-3, a coke control zone distributor 1-4, a baffle 1-5, a first gas-solid separation unit 1-6, a coke controlled catalyst delivery pipe 1-7, a coke control zone gas delivery pipe 1-8, a second gas-solid separation unit 1-9, a first gas collection chamber 1-10, a product gas delivery pipe 1-11, a first stripper 1-12, a spent catalyst slide valve 1-13, and a spent catalyst delivery pipe 1-14; and the spent catalyst slide valve 1-13 is configured to control a circulation volume of a spent catalyst.

The reaction zone distributor 1-2 is located at a bottom of the reaction zone of the fluidized bed reactor 1, and the fluidized bed reactor cooler 1-3 is located in the reaction zone.

Figure 2:
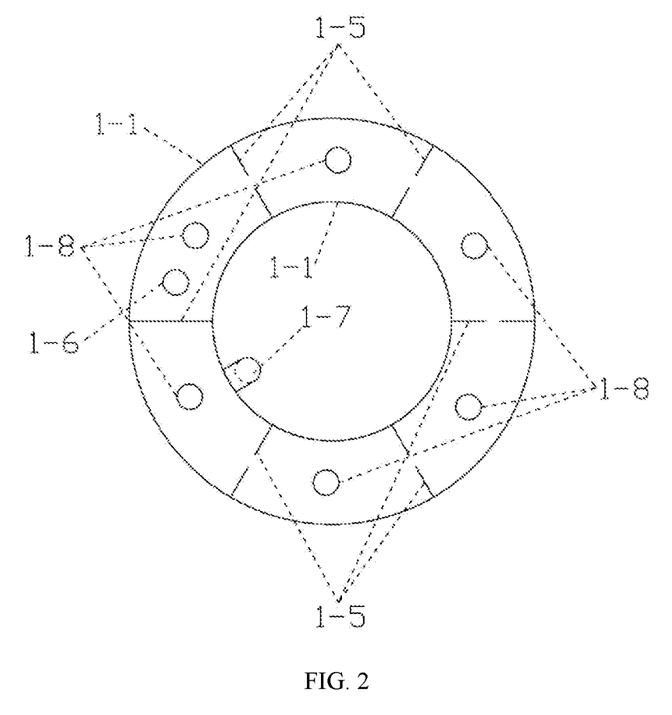
FIG. 2 is a schematic diagram of a cross section of a coke control zone of the fluidized bed reactor according to an embodiment of the present application.

The coke control zone is located in an annular zone above the reaction zone, n baffles 1-5 are arranged in the coke control zone, and the baffles 1-5 divide the coke control zone into n coke control zone subzones, where n is an integer and 2≤n≤10; a bottom of each of the coke control zone subzones is independently provided with a coke control zone distributor 1-4; a cross section of the coke control zone is annular, and a cross section of each of the coke control zone subzones is sector-annular; the $1^{st}$ to $n^{th}$ coke control zone subzones are concentrically arranged in sequence; and a catalyst circulation hole is formed in the baffles 1-5, but no catalyst circulation hole is formed in a baffle shared by the $1^{st}$ coke control zone subzone and the $n^{th}$ coke control zone subzone.

The first gas-solid separation unit 1-6 is located in the gas-solid separation zone of the fluidized bed reactor 1; an inlet of the first gas-solid separation unit 1-6 is connected to an outlet of the regenerated catalyst delivery pipe 2-9, a gas outlet of the first gas-solid separation unit 1-6 is formed in the gas-solid separation zone, and a catalyst outlet of the first gas-solid separation unit 1-6 is formed in the $1^{st}$ coke control zone subzone; and an inlet of the coke controlled catalyst delivery pipe 1-7 is connected to the $n^{th}$ coke control zone subzone, and an outlet of the coke controlled catalyst delivery pipe 1-7 is formed in the reaction zone.

A top of each of the coke control zone subzones is independently provided with a coke control zone gas delivery pipe 1-8, and an outlet of the coke control zone gas delivery pipe 1-8 is formed in the gas-solid separation zone; the second gas-solid separation unit 1-9 and the first gas collection chamber 1-10 are located in the gas-solid separation zone of the fluidized bed reactor 1; an inlet of the second gas-solid separation unit 1-9 is formed in the gas-solid separation zone of the fluidized bed reactor 1, a gas outlet of the second gas-solid separation unit 1-9 is connected to the first gas collection chamber 1-10, and a catalyst outlet of the second gas-solid separation unit 1-9 is formed in the reaction zone; the product gas delivery pipe 1-11 is connected to a top of the first gas collection chamber 1-10; the first stripper 1-12 is located below the fluidized bed reactor 1, an inlet pipe of the first stripper 1-12 penetrates through a lower fluidized bed reactor shell through the bottom of the fluidized bed reactor 1 and is opened above the reaction zone distributor 1-2; and an inlet of the spent catalyst slide valve 1-13 is connected to an outlet pipe at a bottom of the first stripper 1-12, an outlet of the spent catalyst slide valve 1-13 is connected to an inlet of the spent catalyst delivery pipe 1-14 through a pipeline, and an outlet of the spent catalyst delivery pipe 1-14 is connected to a middle part of the fluidized bed regenerator 2.

In a preferred embodiment, the first gas-solid separation unit 1-6 may be a gas-solid cyclone separator.

In a preferred embodiment, the first gas-solid separation unit 1-6 may be a gas-solid rapid separator.

In a preferred embodiment, the second gas-solid separation unit 1-9 may adopt one or more sets of gas-solid cyclone separators, and each set of gas-solid cyclone separators may include a first-stage gas-solid cyclone separator and a second-stage gas-solid cyclone separator.

A device for preparing low-carbon olefins from an oxygen-containing compound is provided, where the device includes a fluidized bed regenerator 2 for regenerating a catalyst; the fluidized bed regenerator 2 includes a regenerator shell 2-1, a regeneration zone distributor 2-2, a third gas-solid separation unit 2-3, a second gas collection chamber 2-4, a flue gas delivery pipe 2-5, a second stripper 2-6, a regenerator cooler 2-7, a regenerated catalyst slide valve 2-8, and a regenerated catalyst delivery pipe 2-9;

the regeneration zone distributor 2-2 is located at a bottom of the fluidized bed regenerator 2, and the third gas-solid separation unit 2-3 is located at an upper part of the fluidized bed regenerator 2; an inlet of the third gas-solid separation unit 2-3 is formed in an upper part of the fluidized bed regenerator 2, a gas outlet of the third gas-solid separation unit 2-3 is connected to the second gas collection chamber 2-4, and a catalyst outlet of the third gas-solid separation unit 2-3 is formed in a lower part of the fluidized bed regenerator 2; the second gas collection chamber 2-4 is located at a top of the fluidized bed regenerator 2, and the flue gas delivery pipe 2-5 is connected to a top of the second gas collection chamber 2-4;

the second stripper 2-6 is located outside the regenerator shell 2-1, and an inlet pipe of the second stripper 2-6 penetrates through the regenerator shell 2-1 and is opened above the regeneration zone distributor 2-2; the regenerator cooler 2-7 is located in the second stripper 2-6; and an inlet of the regenerated catalyst slide valve 2-8 is connected to a bottom of the second stripper 2-6 through a pipeline, an outlet of the regenerated catalyst slide valve 2-8 is connected to an inlet of the regenerated catalyst delivery pipe 2-9 through a pipeline, and an outlet of the regenerated catalyst delivery pipe 2-9 is connected to an inlet of the first gas-solid separation unit 1-6. The regenerated catalyst slide valve 2-8 is configured to control a circulation volume of a regenerated catalyst.

In a preferred embodiment, the third gas-solid separation unit 2-3 may adopt one or more sets of gas-solid cyclone separators, and each set of gas-solid cyclone separators may include a first-stage gas-solid cyclone separator and a second-stage gas-solid cyclone separator.

According to another aspect of the present application, an MTO method including the method for on-line modification of a DMTO catalyst through a coke control reaction is also provided, including the following steps:

a coke control raw material is fed into the coke control zone of the fluidized bed reactor 1 from the coke control zone distributor 1-4; a regenerated catalyst is fed into the first gas-solid separation unit 1-6 from the regenerated catalyst delivery pipe 2-9 to undergo gas-solid separation, a resulting gas is discharged into the gas-solid separation zone of the fluidized bed reactor 1 through the gas outlet of the first gas-solid separation unit 1-6, and a resulting regenerated catalyst is discharged into the coke control zone of the fluidized bed reactor 1 through the catalyst outlet of the first gas-solid separation unit 1-6; the coke control raw material contacts and chemically reacts with the regenerated catalyst in the coke control zone to generate a coke controlled catalyst and a coke control product gas; the coke controlled catalyst passes through the $1^{st}$ to $n^{th}$ coke control zone subzones in sequence through the catalyst circulation holes on the baffles 1-5, and then enters the reaction zone of the fluidized bed reactor 1 through the coke controlled catalyst delivery pipe 1-7; the coke control product gas enters the gas-solid separation zone of the fluidized bed reactor 1 through the coke control zone gas delivery pipe 1-8; a raw material with an oxygen-containing compound is fed into the reaction zone of the fluidized bed reactor 1 from the reaction zone distributor 1-2 to contact the coke controlled catalyst to generate a stream A with low-carbon olefins and a spent catalyst; the stream A and the coke control product gas are mixed in the gas-solid separation zone to produce a stream B, and the stream B enters the second gas-solid separation unit 1-9 to undergo gas-solid separation to obtain a gas-phase stream C and a solid-phase stream D, where the gas-phase stream C is a low-carbon olefin-containing product gas and the solid-phase stream D is a spent catalyst; the gas-phase stream C enters the first gas collection chamber 1-10, and then enters a downstream working section through the product gas delivery pipe 1-11, and the solid-phase stream D is returned to the reaction zone of the fluidized bed reactor 1; the spent catalyst in the reaction zone enters the fluidized bed reactor stripper 1-12 through the inlet pipe of the first stripper 1-12 to undergo stripping, and then enters a middle part of the fluidized bed regenerator 2 through the spent catalyst slide valve 1-13 and the spent catalyst delivery pipe 1-14;

a regeneration gas is fed from the regeneration zone distributor 2-2 to the bottom of the fluidized bed regenerator 2, and in the fluidized bed regenerator 2, the regeneration gas contacts and chemically reacts with the spent catalyst, such that a part of coke in the spent catalyst is burned and eliminated to generate a stream E with a flue gas and a regenerated catalyst; the stream E enters the third gas-solid separation unit 2-3 to undergo gas-solid separation to obtain a flue gas and a regenerated catalyst; the flue gas enters the second gas collection chamber 2-4, and then enters a downstream flue gas treatment system through the flue gas delivery pipe 2-5; the regenerated catalyst is returned to the bottom of the fluidized bed regenerator 2; and the regenerated catalyst in the fluidized bed regenerator 2 enters the second stripper 2-6 to be stripped and cooled, and then enters the first gas-solid separation unit 1-6 through the regenerated catalyst slide valve 2-8 and the regenerated catalyst delivery pipe 2-9.

In a preferred embodiment, the coke control raw material of the present application may be composed of 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water, and a total content of methanol, ethanol, and water may be greater than or equal to 10 wt %.

In a preferred embodiment, the oxygen-containing compound in the method of the present application may be one from the group consisting of methanol, DME, and a mixture of methanol and DME.

In a preferred embodiment, the regeneration gas in the method of the present application may be 0 wt % to 100 wt % air, 0 wt % to 50 wt % oxygen, 0 wt % to 50 wt % nitrogen, and 0 wt % to 50 wt % water vapor.

In a preferred embodiment, an active component of the catalyst may be an SAPO molecular sieve.

In a preferred embodiment, a coke content in the regenerated catalyst may be less than or equal to 3 wt %.

In a preferred embodiment, a coke content in the coke controlled catalyst may be 4 wt % to 9 wt %, and a quartile deviation of coke content distribution in the coke controlled catalyst may be less than 1 wt %; coke species may include polymethylbenzene and polymethylnaphthalene, and a total mass of the polymethylbenzene and the polymethylnaphthalene may account for greater than or equal to 70 wt % of a total mass of coke; and a mass of coke species with a molecular weight greater than 184 may account for less than or equal to 25 wt % of the total mass of coke.

In a preferred embodiment, a coke content in the spent catalyst may be 9 wt % to 13 wt %, and further preferably, the coke content in the spent catalyst may be 10 wt % to 12 wt %.

In a preferred embodiment, process operating conditions of the coke control zone of the fluidized bed reactor 1 may be as follows: apparent gas linear velocity: 0.1 m/s to 0.5 m/s; reaction temperature: 300° C. to 700° C.; reaction pressure: 100 kPa to 500 kPa; and bed density: 400 kg/m³ to 800 kg/m³.

In a preferred embodiment, process operating conditions of the reaction zone of the fluidized bed reactor 1 may be as follows: apparent gas linear velocity: 0.5 m/s to 2.0 m/s; reaction temperature: 350° C. to 550° C.; reaction pressure: 100 kPa to 500 kPa; and bed density: 150 kg/m³ to 500 kg/m³.

In a preferred embodiment, process operating conditions of the fluidized bed regenerator 2 may be as follows: apparent gas linear velocity: 0.5 m/s to 2.0 m/s; regeneration temperature: 600° C. to 750° C.; regeneration pressure: 100 kPa to 500 kPa; and bed density: 150 kg/m³ to 700 kg/m³.

In the method of the present application, the product gas may be composed of 38 wt % to 57 wt % of ethylene, 37 wt % to 55 wt % of propylene, less than or equal to 5 wt % of $C_4$-$C_6$ hydrocarbon compounds, and less than or equal to 3 wt % of other components; and the other components may be methane, ethane, propane, hydrogen, CO, $CO_2$, and the like, and the total selectivity of ethylene and propylene in the product gas may be 93 wt % to 96 wt %.

In the present application, when the production unit consumption is expressed, a mass of DME in the oxygen-containing compound is equivalently converted into a mass of methanol based on a mass of the element C, and a unit of the production unit consumption is ton of methanol/ton of low-carbon olefins.

In the method of the present application, the production unit consumption may be 2.50 to 2.58 tons of methanol/ton of low-carbon olefins.

Example 1

The device shown in FIG. 1 and FIG. 2 is adopted in this example, where 2 baffles are arranged in the coke control zone in the fluidized bed reactor, that is, n=2; the coke control zone includes 2 coke control zone subzones; and the first gas-solid separation unit is a gas-solid cyclone separator.

Specifically, as shown in FIG. 1, a diameter of a junction between the lower shell and the upper shell gradually increases from bottom to top, such that a diameter of the gas-solid separation zone is larger than a diameter of the reaction zone. The coke control zone is located at the junction of the lower shell and the upper shell. A longitudinal cross section of each of the baffles is in a parallelogram.

In this example, the coke control raw material is a mixture of 6 wt % of butane, 81 wt % of butene, 2 wt % of methanol, and 11 wt % of water; the oxygen-containing compound is methanol; the regeneration gas is air; an active component in the catalyst is an SAPO-34 molecular sieve; a coke content in the regenerated catalyst is about 1 wt %; a coke content in the coke controlled catalyst is about 4 wt %, where a total mass of polymethylbenzene and polymethylnaphthalene accounts for about 85 wt % of a total mass of coke, a mass of coke species with a molecular weight greater than 184 accounts for about 6 wt % of the total mass of coke, and a quartile deviation of a coke content distribution in the coke controlled catalyst is about 0.9 wt %; and a coke content in the spent catalyst is about 9 wt %.

Process operating conditions of the coke control zone of the fluidized bed reactor are as follows: apparent gas linear velocity: about 0.3 m/s, reaction temperature: about 500° C., reaction pressure: about 100 kPa, and bed density: about 600 kg/m³.

Process operating conditions of the reaction zone of the fluidized bed reactor are as follows: apparent gas linear velocity: about 2.0 m/s, reaction temperature: about 550° C., reaction pressure: about 100 kPa, and bed density: about 150 kg/m³.

Process operating conditions of the fluidized bed regenerator are as follows: apparent gas linear velocity: about 0.5 m/s; regeneration temperature: about 700° C.; regeneration pressure: about 100 kPa; and bed density: about 700 kg/m³.

In this example, the product gas is composed of 57 wt % of ethylene, 37 wt % of propylene, 3 wt % of $C_4$-$C_6$ hydrocarbon compounds, and 3 wt % of other components, where the other components include methane, ethane, propane, hydrogen, CO, $CO_2$, and the like; and the production unit consumption is 2.55 tons of methanol/ton of low-carbon olefins.

Example 2

The device shown in FIG. 1 and FIG. 2 is adopted in this example, where 10 baffles are arranged in the coke control zone in the fluidized bed reactor, that is, n=10; the coke control zone includes 10 coke control zone subzones; and the first gas-solid separation unit is a gas-solid cyclone separator.

In this example, the coke control raw material is a mixture of 22 wt % of methane, 24 wt % of ethane, 3 wt % of ethylene, 28 wt % of propane, 4 wt % of propylene, 7 wt % of hydrogen, and 12 wt % of water; the oxygen-containing compound is a mixture of 82 wt % of methanol and 18 wt % of DME; the regeneration gas is a mixture of 50 wt % of air and 50 wt % of water vapor; an active component in the catalyst is an SAPO-34 molecular sieve; a coke content in the regenerated catalyst is about 3 wt %; a coke content in the coke controlled catalyst is about 9 wt %, where a total mass of polymethylbenzene and polymethylnaphthalene accounts for about 78 wt % of a total mass of coke, a mass of coke species with a molecular weight greater than 184 accounts for about 13 wt % of the total mass of coke, and a quartile deviation of a coke content distribution in the coke controlled catalyst is about 0.2 wt %; and a coke content in the spent catalyst is about 13 wt %.

Process operating conditions of the coke control zone of the fluidized bed reactor are as follows: apparent gas linear velocity: about 0.1 m/s, reaction temperature: about 300° C., reaction pressure: about 500 kPa, and bed density: about 800 kg/m$^3$.

Process operating conditions of the reaction zone of the fluidized bed reactor are as follows: apparent gas linear velocity: about 0.5 m/s, reaction temperature: about 350° C., reaction pressure: about 500 kPa, and bed density: about 500 kg/m$^3$.

Process operating conditions of the fluidized bed regenerator are as follows: apparent gas linear velocity: about 2.0 m/s; regeneration temperature: about 600° C.; regeneration pressure: about 500 kPa; and bed density: about 150 kg/m$^3$.

In this example, the product gas is composed of 38 wt % of ethylene, 55 wt % of propylene, 5 wt % of $C_4$-$C_6$ hydrocarbon compounds, and 2 wt % of other components, where the other components include methane, ethane, propane, hydrogen, CO, $CO_2$, and the like; and the production unit consumption is 2.58 tons of methanol/ton of low-carbon olefins.

Example 3

The device shown in FIG. 1 and FIG. 2 is adopted in this example, where 4 baffles are arranged in the coke control zone in the fluidized bed reactor, that is, n=4; the coke control zone includes 4 coke control zone subzones; and the first gas-solid separation unit is a gas-solid rapid separator.

In this example, the coke control raw material is a mixture of 1 wt % of propane, 1 wt % of propylene, 3 wt % of butane, 51 wt % of butene, 3 wt % of pentane, 22 wt % of pentene, 1 wt % of hexane, 7 wt % of hexene, 2 wt % of methanol, and 9 wt % of water; the oxygen-containing compound is DME; the regeneration gas is a mixture of 50 wt % of air and 50 wt % of oxygen; an active component in the catalyst is an SAPO-34 molecular sieve; a coke content in the regenerated catalyst is about 2 wt %; a coke content in the coke controlled catalyst is about 6 wt %, where a total mass of polymethylbenzene and polymethylnaphthalene accounts for about 81 wt % of a total mass of coke, a mass of coke species with a molecular weight greater than 184 accounts for about 15 wt % of the total mass of coke, and a quartile deviation of a coke content distribution in the coke controlled catalyst is about 0.6 wt %; and a coke content in the spent catalyst is about 11 wt %.

Process operating conditions of the coke control zone of the fluidized bed reactor are as follows: apparent gas linear velocity: about 0.4 m/s, reaction temperature: about 700° C., reaction pressure: about 300 kPa, and bed density: about 500 kg/m$^3$.

Process operating conditions of the reaction zone of the fluidized bed reactor are as follows: apparent gas linear velocity: about 1.0 m/s, reaction temperature: about 450° C., reaction pressure: about 300 kPa, and bed density: about 300 kg/m$^3$.

Process operating conditions of the fluidized bed regenerator are as follows: apparent gas linear velocity: about 1.0 m/s; regeneration temperature: about 750° C.; regeneration pressure: about 300 kPa; and bed density: about 360 kg/m$^3$.

In this example, the product gas is composed of 48 wt % of ethylene, 47 wt % of propylene, 3 wt % of $C_4$-$C_6$ hydrocarbon compounds, and 2 wt % of other components, where the other components include methane, ethane, propane, hydrogen, CO, $CO_2$, and the like; and the production unit consumption is 2.53 tons of methanol/ton of low-carbon olefins.

Example 4

The device shown in FIG. 1 and FIG. 2 is adopted in this example, where 6 baffles are arranged in the coke control zone in the fluidized bed reactor, that is, n=6; the coke control zone includes 6 coke control zone subzones; and the first gas-solid separation unit is a gas-solid rapid separator.

In this example, the coke control raw material is a mixture of 5 wt % of butane, 72 wt % of butene, 8 wt % of methanol, and 15 wt % of water; the oxygen-containing compound is methanol; the regeneration gas is a mixture of 50 wt % of air and 50 wt % of nitrogen; an active component in the catalyst is an SAPO-34 molecular sieve; a coke content in the regenerated catalyst is about 2 wt %; a coke content in the coke controlled catalyst is about 6 wt %, where a total mass of polymethylbenzene and polymethylnaphthalene accounts for about 70 wt % of a total mass of coke, a mass of coke species with a molecular weight greater than 184 accounts for about 24 wt % of the total mass of coke, and a quartile deviation of a coke content distribution in the coke controlled catalyst is about 0.3 wt %; and a coke content in the spent catalyst is about 12 wt %.

Process operating conditions of the coke control zone of the fluidized bed reactor are as follows: apparent gas linear velocity: about 0.5 m/s, reaction temperature: about 600° C., reaction pressure: about 200 kPa, and bed density: about 400 kg/m$^3$.

Process operating conditions of the reaction zone of the fluidized bed reactor are as follows: apparent gas linear velocity: about 1.5 m/s, reaction temperature: about 500° C., reaction pressure: about 200 kPa, and bed density: about 200 kg/m$^3$.

Process operating conditions of the fluidized bed regenerator are as follows: apparent gas linear velocity: about 1.5 m/s; regeneration temperature: about 680° C.; regeneration pressure: about 200 kPa; and bed density: about 280 kg/m$^3$.

In this example, the product gas is composed of 53 wt % of ethylene, 43 wt % of propylene, 3 wt % of $C_4$-$C_6$ hydrocarbon compounds, and 1 wt % of other components, where the other components include methane, ethane, propane, hydrogen, CO, $CO_2$, and the like; and the production unit consumption is 2.50 tons of methanol/ton of low-carbon olefins.

Comparative Example

This comparative example is different from Example 4 in that, the coke control reaction is not used for on-line modification of the DMTO catalyst; and the raw material fed into the coke control zone is nitrogen, which is an inert gas and does not change the properties of the regenerated catalyst in the coke control zone, that is, a catalyst entering the reaction zone is the regenerated catalyst.

In this example, the product gas is composed of 43 wt % of ethylene, 39 wt % of propylene, 12 wt % of $C_4$-$C_6$ hydrocarbon compounds, and 6 wt % of other components, where the other components include methane, ethane, propane, hydrogen, CO, $CO_2$, and the like; and the production unit consumption is 2.91 tons of methanol/ton of low-carbon olefins.

This comparative example shows that the on-line modification of a DMTO catalyst through a coke control reaction can greatly improve the performance of the catalyst and reduce the production unit consumption.

The above examples are merely few examples of the present application, and do not limit the present application in any form. Although the present application is disclosed as above with preferred examples, the present application is not limited thereto. Some changes or modifications made by any technical personnel familiar with the profession using the technical content disclosed above without departing from the scope of the technical solutions of the present application are equivalent to equivalent implementation cases and fall within the scope of the technical solutions.

What is claimed is:

1. A fluidized bed reactor, wherein the fluidized bed reactor comprises a main shell and a coke control zone shell;
   the main shell comprises an upper shell and a lower shell;
   the upper shell encloses a first gas-solid separation zone, and the lower shell encloses a reaction zone;
   the reaction zone axially communicates with the first gas-solid separation zone;
   the coke control zone shell is circumferentially arranged on an outer wall of the main shell;
   the coke control zone shell and the main shell enclose an annular cavity, and the annular cavity is a coke control zone;
   n baffles are radially arranged in the coke control zone, and the n baffles divide the coke control zone into n coke control zone subzones, where n is an integer;
   each of the n coke control zone subzones is provided with a coke control raw material inlet; and
   a catalyst circulation hole is formed in each of n−1 of the n baffles, such that a catalyst and a coke control raw material entering the coke control zone flow in an annular direction.

2. The fluidized bed reactor according to claim 1, wherein in the coke control zone, the n baffles comprise a $1^{st}$ baffle, and a $2^{nd}$ baffle to an $n^{th}$ baffle;
   no catalyst circulation hole is formed in the $1^{st}$ baffle;
   the catalyst circulation hole is formed in each of the $2^{nd}$ baffle to the $n^{th}$ baffle;
   a coke control zone catalyst inlet is formed in a $1^{st}$ coke control zone subzone formed through division by the $1^{st}$ baffle and the $2^{nd}$ baffle;
   a coke controlled catalyst delivery pipe is arranged in an $n^{th}$ coke control zone subzone formed through division by the $1^{st}$ baffle and the $n^{th}$ baffle, and an outlet of the coke controlled catalyst delivery pipe is formed in the reaction zone;
   the coke control raw material inlet is formed at bottoms of the coke control zone subzones, and the coke control raw material inlet is a coke control zone distributor; and
   a coke control zone gas delivery pipe is arranged at tops of the coke control zone subzones, and an outlet of the coke control zone gas delivery pipe is formed in the first gas-solid separation zone.

3. The fluidized bed reactor according to claim 1, wherein n has a value range of $2 \leq n \leq 10$;
   a reaction zone distributor is arranged at a bottom of the reaction zone, and the reaction zone distributor is configured to feed a reaction raw material; and
   the reaction zone is provided with a fluidized bed reactor cooler, and the bottom of the reaction zone is provided with a first stripper; an inlet of the first stripper is formed inside the lower shell; an outlet of the first stripper is formed outside the lower shell; an open end of the inlet of the first stripper is located above an outlet end of the coke controlled catalyst delivery pipe; and the outlet end of the coke controlled catalyst delivery pipe is located above the reaction zone distributor.

4. The fluidized bed reactor according to claim 1, wherein the first gas-solid separation zone is provided with a first gas-solid separation unit and a second gas-solid separation unit;
   a catalyst outlet pipe of the first gas-solid separation unit penetrates through a top of the coke control zone and is inserted in a $1^{st}$ coke control zone subzone;
   a gas outlet of the first gas-solid separation unit is formed in the first gas-solid separation zone;
   an inlet of the second gas-solid separation unit is formed in the first gas-solid separation zone; and
   a catalyst outlet end of the second gas-solid separation unit is located in the reaction zone;
   wherein a first gas collection chamber is arranged in an upper part of the first gas-solid separation zone; a gas outlet of the second gas-solid separation unit communicates with the first gas collection chamber; and the first gas collection chamber further communicates with a product gas delivery pipe.

5. A device for preparing low-carbon olefins from an oxygen-containing compound, wherein the device comprises a fluidized bed regenerator and the fluidized bed reactor according to claim 1.

6. The device according to claim 5, wherein the fluidized bed regenerator comprises a regenerator shell; the regenerator shell comprises an upper regenerator shell and a lower regenerator shell; the upper regenerator shell encloses a second gas-solid separation zone, and the lower regenerator shell encloses a regeneration zone;
   a spent catalyst inlet is formed in the regenerator shell; and
   the spent catalyst inlet communicates with a first stripper outlet pipe through a spent catalyst delivery pipe.

7. The device according to claim 6, wherein a regeneration zone distributor is arranged at a bottom of the regeneration zone; and
   the regeneration zone distributor is configured to feed a regeneration gas;
   wherein a second stripper is arranged at the bottom of the regeneration zone; an inlet of the second stripper is formed inside the regenerator shell; an outlet of the second stripper is formed outside the regenerator shell; the second stripper communicates with a first gas-solid separation unit through a regenerated catalyst delivery pipe; and an open end of the inlet of the second stripper is located above the regeneration zone distributor.

8. The device according to claim 6, wherein a third gas-solid separation unit and a second gas collection chamber are arranged in the regenerator shell;
   the second gas collection chamber is located at an inner top of the regenerator shell;
   a gas outlet of the third gas-solid separation unit communicates with the second gas collection chamber;
   the second gas collection chamber communicates with a flue gas delivery pipe; and
   a catalyst outlet end of the third gas-solid separation unit is located above an open end of a second stripper inlet pipe.

9. A method for preparing low-carbon olefins, wherein the method for preparing low-carbon olefins comprises preparing low-carbon olefins using the device according to claim 5;
the method for preparing low-carbon olefins comprises preparing low-carbon olefins from an oxygen-containing compound, wherein an on-line modification of a dimethyl ether/methanol to olefins (DMTO) catalyst through a coke control reaction is performed using the fluidized bed reactor; wherein the method comprises the following step: feeding a catalyst and a coke control raw material into the coke control zone, wherein the catalyst reacts with the coke control raw material while flowing in an annular direction along the coke control zone subzones to generate a product comprising a coke controlled catalyst, and the coke controlled catalyst is a modified DMTO catalyst;
the method for preparing the low-carbon olefins further comprises the following steps:
allowing a spent catalyst in the reaction zone of the fluidized bed reactor to enter the fluidized bed regenerator and undergo a regeneration treatment to generate a regenerated catalyst, and allowing the regenerated catalyst to enter the coke control zone of the fluidized bed reactor and to contact and react with the coke control raw material.

10. The method according to claim 9, wherein the method comprises: allowing the spent catalyst in the reaction zone to enter the fluidized bed regenerator through a first stripper and a spent catalyst delivery pipe, and to contact and react with a regeneration gas to obtain a first stream with a flue gas and the regenerated catalyst; allowing the first stream to enter a third gas-solid separation unit to separate the flue gas and the regenerated catalyst; and
allowing the separated regenerated catalyst to enter the coke control zone of the fluidized bed reactor through a second stripper, a regenerated catalyst delivery pipe, and a first gas-solid separation unit, and to contact and react with the coke control raw material.

11. The method according to claim 10, wherein a coke content in the regenerated catalyst is less than or equal to 3 wt %;
the regeneration gas is at least one selected from the group consisting of oxygen, nitrogen, water vapor, and air;
the regeneration gas comprises 0 wt % to 100 wt % of air, 0 wt % to 50 wt % of oxygen, 0 wt % to 50 wt % of nitrogen, and 0 wt % to 50 wt % of water vapor; and
contents of the air, the oxygen, the nitrogen, and the water vapor are not simultaneously zero.

12. The method according to claim 9, wherein process conditions of the regeneration zone are as follows: apparent gas linear velocity: 0.5 m/s to 2.0 m/s; regeneration temperature: 600° C. to 750° C.; regeneration pressure: 100 kPa to 500 kPa; and bed density: 150 kg/m³ to 700 kg/m³.

13. The method according to claim 9, wherein the catalyst flows in the annular direction along the catalyst circulation hole on each of n−1 of the n baffles; and the coke control raw material enters the n coke control zone subzones from the coke control zone distributor to react with the catalyst;
wherein the coke controlled catalyst prepared enters the reaction zone through the coke controlled catalyst delivery pipe, and then contacts and reacts with a raw material comprising the oxygen-containing compound fed through a reaction zone distributor to generate a second stream with low-carbon olefins and a spent catalyst; and the product further comprises a coke control product gas, and the coke control product gas enters the first gas-solid separation zone through a coke control zone gas delivery pipe;
wherein the second stream is mixed with the coke control product gas entering the first gas-solid separation zone to produce a third stream; the third stream enters a second gas-solid separation unit to undergo gas-solid separation to obtain a gas-phase stream and a solid-phase stream; the gas-phase stream is a low-carbon olefin-containing product gas; and the solid-phase stream comprises the spent catalyst;
wherein the gas-phase stream enters a first gas collection chamber, and then enters a downstream working section through a product gas delivery pipe; the solid-phase stream is returned to the reaction zone of the fluidized bed reactor; and the catalyst in the reaction zone enters a first stripper through an open end of a first stripper inlet pipe to undergo stripping, and then enters a downstream zone.

14. The method according to claim 9, wherein the coke control raw material comprises $C_1$-$C_6$ hydrocarbon compounds;
the hydrocarbon compounds are at least one selected from the group consisting of $C_1$-$C_6$ alkanes and $C_1$-$C_6$ olefins;
the coke control raw material further comprises at least one selected from the group consisting of hydrogen, an alcohol compound, and water; and a proportion of a total mass of the alcohol compound and the water in a mass of the coke control raw material is greater than or equal to 10 wt % and less than or equal to 50 wt %;
the alcohol compound is at least one selected from the group consisting of methanol and ethanol; and
the coke control raw material comprises 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water;
and a total amount of the hydrocarbon compounds is greater than 0%.

15. The method according to claim 9, wherein the catalyst comprises an SAPO molecular sieve;
a coke content in the catalyst is less than or equal to 3 wt %;
a coke content in the coke controlled catalyst is 4 wt % to 9 wt %; and
a quartile deviation of a coke content distribution in the coke controlled catalyst is less than 1 wt %.

16. The method according to claim 9, wherein coke species in the coke controlled catalyst comprise polymethylbenzene and polymethylnaphthalene;
a total mass of the polymethylbenzene and the polymethylnaphthalene accounts for greater than or equal to 70 wt % of a total mass of coke;
a mass of coke species with a molecular weight greater than 184 accounts for less than or equal to 25 wt % of the total mass of coke; and
the total mass of coke refers to a total mass of coke species.

17. The method according to claim 13, wherein a coke content in the spent catalyst is 9 wt % to 13 wt %.

18. The method according to claim 13, wherein the oxygen-containing compound is at least one selected from the group consisting of methanol and dimethyl ether (DME).

19. The method according to claim 9, wherein process conditions of the coke control zone are as follows: apparent gas linear velocity: 0.1 m/s to 0.5 m/s; reaction temperature: 300° C. to 700° C.; reaction pressure: 100 kPa to 500 kPa; and bed density: 400 kg/m$^3$ to 800 kg/m$^3$.

20. The method according to claim 13, wherein process conditions of the reaction zone are as follows: apparent gas linear velocity: 0.5 m/s to 2.0 m/s; reaction temperature: 350° C. to 550° C.; reaction pressure: 100 kPa to 500 kPa; and bed density: 150 kg/m$^3$ to 500 kg/m$^3$.

* * * * *